United States Patent
Cohn et al.

(10) Patent No.: US 12,102,372 B2
(45) Date of Patent: Oct. 1, 2024

(54) TISSUE RESECTION APPARATUS

(71) Applicant: Prana Thoracic, Inc., Houston, TX (US)

(72) Inventors: William Cohn, Bellaire, TX (US); Jonathan Melchor, Warwick, RI (US); Steven Nguyen, Cypress, TX (US)

(73) Assignee: Prana Thoracic, Inc., Houston, TX (US)

( * ) Notice: Subject to any disclaimer, the term of this patent is extended or adjusted under 35 U.S.C. 154(b) by 0 days.

(21) Appl. No.: 18/335,975

(22) Filed: Jun. 15, 2023

(65) Prior Publication Data
US 2023/0380878 A1 Nov. 30, 2023

Related U.S. Application Data

(63) Continuation of application No. 16/512,616, filed on Jul. 16, 2019, now abandoned.
(Continued)

(51) Int. Cl.
*A61B 18/14* (2006.01)
*A61B 10/02* (2006.01)
(Continued)

(52) U.S. Cl.
CPC ........ *A61B 18/082* (2013.01); *A61B 10/0266* (2013.01); *A61B 10/04* (2013.01);
(Continued)

(58) Field of Classification Search
CPC ....... A61B 18/08; A61B 18/082; A61B 18/14; A61B 18/1402; A61B 18/148; A61B 18/1482; A61B 2018/00577; A61B 2018/00595; A61B 2018/00601; A61B 2018/00196; A61B 2018/00273;
(Continued)

(56) References Cited

U.S. PATENT DOCUMENTS

| 4,007,732 A | 2/1977 | Kvavle et al. |
| 4,735,194 A | 4/1988 | Stiegmann |

(Continued)

FOREIGN PATENT DOCUMENTS

| CN | 1221603 A | 7/1999 |
| CN | 102656171 A | 9/2012 |

(Continued)

OTHER PUBLICATIONS

Extended European Search Report for European Application No. EP19189128 dated Oct. 9, 2019, 4 pages.
(Continued)

*Primary Examiner* — Thomas A Giuliani
(74) *Attorney, Agent, or Firm* — COOLEY LLP

(57) ABSTRACT

A tissue resection apparatus is provided which includes an outer tube with a helical coil disposed on a distal end. The coil is provided with a first electrode. A central tube has a distal edge profile comprising one or more surface segments. One of the surface segments includes a second electrode. The central tube is slidably disposed within the outer tube and positioned such that second electrode opposes at least a portion of the first electrode. A cutting tube is slidably disposed within the central tube and includes a cutting edge.

29 Claims, 5 Drawing Sheets

Related U.S. Application Data

(60) Provisional application No. 62/756,234, filed on Nov. 6, 2018, provisional application No. 62/749,302, filed on Oct. 23, 2018, provisional application No. 62/744,797, filed on Oct. 12, 2018, provisional application No. 62/728,170, filed on Sep. 7, 2018, provisional application No. 62/712,545, filed on Jul. 31, 2018.

(51) Int. Cl.
*A61B 10/04* (2006.01)
*A61B 17/34* (2006.01)
*A61B 18/08* (2006.01)
*A61B 18/12* (2006.01)
*A61B 18/00* (2006.01)

(52) U.S. Cl.
CPC ...... *A61B 17/3403* (2013.01); *A61B 17/3423* (2013.01); *A61B 18/1206* (2013.01); *A61B 2010/045* (2013.01); *A61B 2018/00541* (2013.01); *A61B 2018/00577* (2013.01); *A61B 2018/00595* (2013.01); *A61B 2018/00601* (2013.01); *A61B 2018/126* (2013.01)

(58) Field of Classification Search
CPC ........... A61B 2018/00404; A61B 2018/00428; A61B 2018/00541; A61B 2018/00607; A61B 2018/126; A61B 2018/1407; A61B 2018/141; A61B 2018/1435; A61B 10/0266; A61B 2010/045
USPC ........ 606/37, 39, 40, 41, 45, 48–50; 607/98, 607/99, 101, 113, 115, 116; 600/566
See application file for complete search history.

(56) References Cited

U.S. PATENT DOCUMENTS

| | | | |
|---|---|---|---|
| 5,133,360 A | 7/1992 | Spears | |
| 5,190,561 A | 3/1993 | Graber | |
| 5,196,024 A | 3/1993 | Barath | |
| 5,353,804 A | 10/1994 | Kornberg et al. | |
| 5,507,743 A | 4/1996 | Edwards et al. | |
| 5,643,282 A | 7/1997 | Kieturakis | |
| 5,651,788 A | 7/1997 | Fleischer et al. | |
| 5,681,281 A | 10/1997 | Vigil et al. | |
| 5,779,698 A | 7/1998 | Clayman et al. | |
| 5,810,811 A | 9/1998 | Yates et al. | |
| 5,843,108 A | 12/1998 | Samuels | |
| 5,882,316 A | 3/1999 | Chu et al. | |
| 5,908,435 A | 6/1999 | Samuels | |
| 5,928,163 A | 7/1999 | Roberts et al. | |
| 5,961,526 A | 10/1999 | Chu et al. | |
| 6,022,362 A | 2/2000 | Lee et al. | |
| 6,213,957 B1 | 4/2001 | Milliman et al. | |
| 6,258,108 B1 | 7/2001 | Lary | |
| 6,493,589 B1 | 12/2002 | Medhkour et al. | |
| 6,574,513 B1 | 6/2003 | Collura et al. | |
| 6,652,520 B2 | 11/2003 | Moorman et al. | |
| 6,770,070 B1 | 8/2004 | Balbierz | |
| 6,974,467 B1 | 12/2005 | Gonzales, Jr. | |
| 7,517,352 B2 | 4/2009 | Evans et al. | |
| 7,811,303 B2 | 10/2010 | Fallin et al. | |
| 8,239,030 B1 | 8/2012 | Hagedorn et al. | |
| 8,506,503 B2 | 8/2013 | Fritscher-Ravens et al. | |
| 8,602,973 B2 | 12/2013 | Wendlandt | |
| 8,734,362 B2 | 5/2014 | Boyle, Jr. | |
| 9,895,190 B2 | 2/2018 | Trieu | |
| 10,022,179 B2 | 7/2018 | Feinberg et al. | |
| 10,039,529 B2 | 8/2018 | Kerr et al. | |
| 10,314,578 B2 | 6/2019 | Leimbach et al. | |
| 10,413,368 B2 | 9/2019 | Nilsagard et al. | |
| 10,555,769 B2 | 2/2020 | Worrell et al. | |
| 10,595,835 B2 | 3/2020 | Kerr et al. | |
| 11,103,272 B2 | 8/2021 | Boyle et al. | |
| 11,331,087 B2 | 5/2022 | Boyle, Jr. | |
| 11,723,708 B2 | 8/2023 | Cohn et al. | |
| 2002/0019597 A1 | 2/2002 | Dubrul et al. | |
| 2002/0059938 A1 | 5/2002 | Fogarty et al. | |
| 2002/0082614 A1 | 6/2002 | Logan et al. | |
| 2002/0095101 A1 | 7/2002 | Fontenot | |
| 2003/0129382 A1 | 7/2003 | Treat | |
| 2003/0233099 A1 | 12/2003 | Danaek et al. | |
| 2004/0010206 A1 | 1/2004 | Dubrul et al. | |
| 2004/0122349 A1 | 6/2004 | Lafontaine et al. | |
| 2004/0133254 A1 | 7/2004 | Sterzer et al. | |
| 2004/0147917 A1 | 7/2004 | Mueller et al. | |
| 2004/0215296 A1 | 10/2004 | Ganz et al. | |
| 2004/0254572 A1* | 12/2004 | McIntyre | A61B 18/1477 606/41 |
| 2005/0113854 A1 | 5/2005 | Uckele | |
| 2005/0288695 A1 | 12/2005 | Jenson et al. | |
| 2006/0009756 A1 | 1/2006 | Francischelli et al. | |
| 2006/0025815 A1 | 2/2006 | McGurk et al. | |
| 2006/0069388 A1 | 3/2006 | Truckai et al. | |
| 2006/0074484 A1 | 4/2006 | Huber | |
| 2006/0190037 A1 | 8/2006 | Ginn et al. | |
| 2007/0015984 A1 | 1/2007 | Yeo et al. | |
| 2007/0043350 A1 | 2/2007 | Soltesz et al. | |
| 2007/0073343 A1 | 3/2007 | Jahns et al. | |
| 2007/0123852 A1 | 5/2007 | Deem et al. | |
| 2007/0156156 A1 | 7/2007 | Badie | |
| 2007/0179494 A1* | 8/2007 | Faure | A61B 18/1477 606/41 |
| 2008/0110457 A1 | 5/2008 | Barry et al. | |
| 2009/0054805 A1 | 2/2009 | Boyle, Jr. | |
| 2009/0105745 A1 | 4/2009 | Culbert | |
| 2010/0036312 A1 | 2/2010 | Krolik et al. | |
| 2010/0168821 A1 | 7/2010 | Johnson et al. | |
| 2010/0174306 A1 | 7/2010 | Mitelberg et al. | |
| 2011/0105841 A1 | 5/2011 | Kutikov et al. | |
| 2011/0105947 A1 | 5/2011 | Fritscher-Ravens et al. | |
| 2011/0190764 A1 | 8/2011 | Long et al. | |
| 2012/0071866 A1 | 3/2012 | Kerr et al. | |
| 2012/0071922 A1 | 3/2012 | Shanley et al. | |
| 2012/0143020 A1 | 6/2012 | Bordoley et al. | |
| 2012/0253229 A1 | 10/2012 | Cage | |
| 2012/0316608 A1 | 12/2012 | Foley | |
| 2013/0018414 A1 | 1/2013 | Widomski et al. | |
| 2013/0046140 A1 | 2/2013 | Pravong et al. | |
| 2013/0150701 A1 | 6/2013 | Budar et al. | |
| 2013/0190809 A1 | 7/2013 | Vidlund et al. | |
| 2013/0197357 A1 | 8/2013 | Green et al. | |
| 2014/0236184 A1 | 8/2014 | Leimbach et al. | |
| 2014/0276009 A1 | 9/2014 | Boyle, Jr. | |
| 2014/0276687 A1 | 9/2014 | Goodman et al. | |
| 2014/0276911 A1 | 9/2014 | Smith et al. | |
| 2014/0277039 A1 | 9/2014 | Liberatore et al. | |
| 2014/0277071 A1 | 9/2014 | Wu et al. | |
| 2015/0057570 A1 | 2/2015 | Chin et al. | |
| 2015/0112225 A1 | 4/2015 | Prow et al. | |
| 2015/0265331 A1 | 9/2015 | Fleury et al. | |
| 2015/0342638 A1 | 12/2015 | Smith et al. | |
| 2016/0067465 A1 | 3/2016 | Gerrans et al. | |
| 2016/0220294 A1 | 8/2016 | Babkin et al. | |
| 2016/0367279 A1* | 12/2016 | Orphanos | A61B 17/3417 |
| 2017/0042516 A1 | 2/2017 | Boyle, Jr. | |
| 2017/0281214 A1 | 10/2017 | Brown et al. | |
| 2018/0140319 A1 | 5/2018 | Saidi et al. | |
| 2018/0193060 A1 | 7/2018 | Reddy et al. | |
| 2019/0038306 A1 | 2/2019 | Lindner et al. | |
| 2019/0076164 A1 | 3/2019 | Boyle, Jr. et al. | |
| 2019/0099197 A1 | 4/2019 | Boyle, Jr. et al. | |
| 2019/0201029 A1 | 7/2019 | Shelton, IV et al. | |
| 2019/0269387 A1 | 9/2019 | Kerr | |
| 2019/0388132 A1 | 12/2019 | Azamian et al. | |
| 2020/0038089 A1 | 2/2020 | Cohn et al. | |
| 2020/0038090 A1 | 2/2020 | Cohn et al. | |
| 2020/0038097 A1* | 2/2020 | Cohn | A61B 17/3209 |
| 2020/0390427 A1 | 12/2020 | Eisenthal et al. | |
| 2021/0219967 A1 | 7/2021 | Cohn et al. | |
| 2021/0322091 A1 | 10/2021 | Addison et al. | |

(56) References Cited

U.S. PATENT DOCUMENTS

| | | |
|---|---|---|
| 2021/0338215 A1 | 11/2021 | Cohn et al. |
| 2021/0338218 A1 | 11/2021 | Cohn et al. |
| 2021/0338265 A1 | 11/2021 | Cohn et al. |
| 2021/0338315 A1 | 11/2021 | Cohn et al. |
| 2021/0338316 A1 | 11/2021 | Cohn et al. |
| 2021/0378731 A1 | 12/2021 | Boateng et al. |
| 2021/0393332 A1 | 12/2021 | Cohn et al. |
| 2022/0031382 A1 | 2/2022 | Cohn et al. |
| 2022/0047314 A1 | 2/2022 | Cohn et al. |
| 2022/0047322 A1 | 2/2022 | Cohn et al. |
| 2022/0225970 A1 | 7/2022 | Boyle, Jr. |

FOREIGN PATENT DOCUMENTS

| | | |
|---|---|---|
| DE | 102016101915 A1 | 8/2017 |
| EP | 1340469 A1 | 9/2003 |
| EP | 2866700 A1 | 5/2015 |
| EP | 3603546 A1 | 2/2020 |
| JP | H11244298 A | 9/1999 |
| JP | 3287788 B2 | 6/2002 |
| JP | 2003516800 A | 5/2003 |
| JP | 2004528056 A | 9/2004 |
| JP | 2007185495 A | 7/2007 |
| JP | 2008538518 A | 10/2008 |
| JP | 2012500098 A | 1/2012 |
| JP | 2012183302 A | 9/2012 |
| JP | 2013509255 A | 3/2013 |
| JP | 2014113211 A | 6/2014 |
| JP | 2019505320 A | 2/2019 |
| WO | WO-9603163 A1 | 2/1996 |
| WO | WO-2005110508 A2 | 11/2005 |
| WO | WO-2006108067 A2 | 10/2006 |
| WO | WO-2007014313 A2 | 2/2007 |
| WO | WO-2010001405 A1 | 1/2010 |
| WO | WO-2011053648 A1 | 5/2011 |
| WO | WO-2011094110 A1 | 8/2011 |
| WO | WO-2014172396 A2 | 10/2014 |
| WO | WO-2018144898 A1 | 8/2018 |
| WO | WO-2018218210 A1 | 11/2018 |
| WO | WO-2019130110 A1 | 7/2019 |
| WO | WO-2019239338 A2 | 12/2019 |
| WO | WO-2020006660 A1 | 1/2020 |
| WO | WO-2021220220 A1 | 11/2021 |
| WO | WO-2021220221 A2 | 11/2021 |
| WO | WO-2021220222 A2 | 11/2021 |
| WO | WO-2021220223 A1 | 11/2021 |
| WO | WO-2021220224 A2 | 11/2021 |
| WO | WO-2021220225 A1 | 11/2021 |
| WO | WO-2021250526 A1 | 12/2021 |
| WO | WO-2021260468 A1 | 12/2021 |
| WO | WO-2022023998 A1 | 2/2022 |
| WO | WO-2022034412 A1 | 2/2022 |
| WO | WO-2022038433 A1 | 2/2022 |
| WO | WO-2022214896 A1 | 10/2022 |

OTHER PUBLICATIONS

Extended European Search Report for European Application No. EP19189139 dated Oct. 9, 2019, 7 pages.
Final office action for U.S. Appl. No. 16/512,649, mailed Jan. 20, 2023, 10 pages.
Final office action for U.S. Appl. No. 16/512,649, mailed Mar. 14, 2022, 10 pages.
Indian Office Action for Indian Application No. IN201914029519 dated Sep. 23, 2022, 9 pages.
Indian Office Action for Indian Patent Application No. IN201914029517 dated Sep. 27, 2022, 8 pages.
Indian Office Action for Indian Patent Application No. IN201914029518 dated Oct. 28, 2022, 5 pages.
International Search Report and Written Opinion for Application No. PCT/IB2021/053588, mailed Jul. 1, 2021, 11 pages.
International Search Report and Written Opinion for Application No. PCT/IB2022/052603, mailed Jun. 10, 2021, 12 pages.
Japanese Office Action for Japanese Application No. JP2019139537 dated Jun. 6, 2023, 3 pages.
Non final office action for U.S. Appl. No. 16/512,616, mailed Dec. 15, 2022, 10 pages.
Non final office action for U.S. Appl. No. 16/512,649, mailed Jul. 25, 2022, 11 pages.
Non final office action for U.S. Appl. No. 16/512,649, mailed Sep. 21, 2021, 10 pages.
Non-Final Office Action for U.S. Appl. No. 16/512,628 dated Sep. 22, 2022, 7 pages.
Office Action for Japanese Application No. JP2019139478 dated May 21, 2023, 5 pages.
Non-Final Office Action for U.S. Appl. No. 18/335,975 dated Oct. 23, 2023, 17 pages.
Office Action for Brazilian Application No. BR102019015643 mailed Dec. 26, 2023, 5 pages.
Office Action for Japanese Application No. JP20190139478 dated Nov. 15, 2023, 9 pages.
Restriction Requirement for U.S. Appl. No. 17/226,738 mailed Feb. 13, 2024, 7 pages.
Non-Final Office Action for U.S. Appl. No. 17/368,992 mailed Jun. 18, 2024, 9 pages.

* cited by examiner

TISSUE RESECTION APPARATUS

CROSS-REFERENCES TO OTHER RELATED PATENT APPLICATIONS

This application is a continuation of U.S. patent application Ser. No. 16/512,616, filed Jul. 16, 2019, now abandoned, which claims priority to (1) U.S. Provisional Application No. 62/712,545, filed Jul. 31, 2018, (2) U.S. Provisional Application No. 62/728,170, filed Sep. 7, 2018, (3) U.S. Provisional Application No. 62/744,797, filed Oct. 12, 2018, (4) U.S. Provisional Application No. 62/749,302, filed Oct. 23, 2018, and (5) U.S. Provisional Application No. 62/756,234, filed Nov. 6, 2018, the disclosures of each of which are incorporated herein by reference in their entireties.

BACKGROUND OF THE INVENTION

1. Field of the Invention

The present invention relates to a system, device and method for tissue resection. More particularly, the present invention relates to a system, device and method for lesion removal.

2. Discussion of the Related Art

Cancer is not a single disease, but rather a collection of related diseases that can start essentially anywhere in the body. Common amongst all types of cancer is that the body's cells begin to divide without stopping, proliferating and potentially spreading into surrounding tissues. In the normal course of events, cells grow and divide to form new cells as required by the body and when they become damaged or old, they die, and new cells replace the damaged or old cells; however, cancer interrupts this process. With cancer, the cells become abnormal, and cells that should die do not and new cells form when they are not needed. These new cells can reproduce or proliferate without stopping and may form growths called tumors.

Cancerous tumors are malignant, which means they can spread into or invade surrounding healthy tissue. In addition, cancer cells can break off and travel to remote areas in the body through blood or in the lymph system.

Benign tumors, unlike malignant tumors, do not spread or invade surrounding tissue; however, they may grow large and cause damage. Both malignant and benign tumors may be removed or treated. Malignant tumors tend to grow back whereas benign tumors can grow back but are much less likely to do so.

Cancer is a genetic disease in that it is caused by changes in the genes that control the ways that cells function, especially in how they grow and divide. Genetic changes that cause cancer may be inherited or they may arise over an individual's lifetime as a result of errors that occur as cells divide or because of damage to DNA caused by certain environmental exposure, for example, industrial/commercial chemicals and ultraviolet light. The genetic changes that may cause cancer tend to affect three types of genes; namely proto-oncogenes which are involved in normal cell growth and division, tumor suppressor genes which are also involved in controlling cell growth and division, and DNA repair genes which, as the name implies, are involved in repairing damaged DNA.

More than one-hundred distinct types of cancer have been identified. The type of cancer may be named for the organ or tissue where the cancers arise, for example, lung cancer, or the type of cell that formed them, for example squamous cell cancer. Cancer, unfortunately, is a leading cause of death both in the United States and world-wide. According to the World Health Organization, the number of new cancer cases will rise to twenty-five (25) million per year over the next two decades.

Lung cancer is one of the most common cancers today. According to the World Cancer Report 2014 from the World Health Organization, lung cancer occurred in 14 million people and resulted in 8.8 million deaths world-wide, making it the most common cause of cancer-related death in men and the second most common cause of cancer-related death in women. Lung cancer or lung carcinoma is a malignant lung tumor that if left untreated can metastasize into neighboring tissues and organs. The majority of lung cancer is caused by long-term tobacco smoking; however, about 10 to 15 percent of lung cancer cases are not tobacco related. These non-tobacco cases are most often caused by a combination of genetic factors and exposure to certain environmental conditions, including radon gas, asbestos, second-hand tobacco smoke, other forms of air pollution, and other agents. The chance of surviving lung cancer as well as other forms of cancer depends on early detection and treatment.

When a lesion is detected in the lungs, a biopsy is performed and sent for study. If it is determined that the lesion is cancerous, a second procedure may be performed to remove the cancer. If the biopsy reveals no cancer, it may be correct, or the biopsy did not pick the cancerous cells. Accordingly, there exists a need for removing the whole lesion in one single procedure so that an accurate diagnosis may be performed.

SUMMARY OF THE INVENTION

The system, device and method for performing lung lesion removal of the present invention overcomes the limitations associated with the prior art.

The present invention relates to a system, device and method for performing lung lesion removal. A lung needle biopsy is typically performed when an abnormality is found on an imaging test, for example, an X-ray or CAT scan. In a lung needle biopsy, a fine needle is used to remove sample of lung tissue for examining under a microscope to determine the presence of abnormal cells. Tissue diagnosis is challenging in small (<6 mm) and intermediate (6-12 mm) nodules. CT guided biopsy of peripheral lesions, either through the chest wall (80%) or by means of a bronchoscope (20%) yields only a 0.001-0.002 cm 2 of diagnostic tissue, and as such, cancer, when present, is only successfully identified in 60% of small and intermediate nodules. Although bronchoscopic techniques and technology continue to evolve, biopsy accuracy, specificity, and sensitivity will always be limited when dealing with small and intermediate nodules in the periphery of the lung.

If it is determined that the lesion is cancerous, a second procedure may be performed to remove the lesion and then followed up with chemotherapy and/or radiation. The second procedure most likely involves lung surgery. These procedures are typically done through an incision between the ribs. There are a number of possible procedures depending on the state of the cancer. Video-assisted thoracic surgery is a less invasive procedure for certain types of lung cancer. It is performed through small incisions utilizing an endoscopic approach and is typically utilized for performing wedge resections of smaller lesions close to the surface of a lung. In a wedge resection, a portion of the lobe is removed.

In a sleeve resection, a portion of a large airway is removed thereby preserving more lung function.

Nodules deeper than 2-3 cm from the lung surface, once identified as suspicious for cancer, are difficult to localize and excise using laparoscopic or robotic lung sparing technique despite pre-procedure image guided biopsy and localization. Thus, surgeons perform an open thoracotomy or lobectomy to remove lung nodules that are 2-3 cm from the lung surface. A thoracotomy is an open approach surgery in which a portion of a lobe, a full lobe or an entire lung is removed. In a pneumonectomy, an entire lung is removed. This type of surgery is obviously the most aggressive. In a lobectomy, an entire section or lobe of a lung is removed and represents a less aggressive approach than removing the entire lung. All thoracoscopic lung surgeries require trained and experienced thoracic surgeons and the favorability of surgical outcomes track with operative experience.

Any of these types of lung surgery is a major operation with possible complications which depend on the extent of the surgery as well as the patient's overall health. In addition to the reduction in lung function associated with any of these procedures, the recovery may take from weeks to months. With a thoracotomy, spreading of the ribs is required, thereby increasing postoperative pain. Although video-assisted thoracic surgery is less invasive, there can still be a substantial recovery period. In addition, once the surgery is complete, full treatment may require a system chemotherapy and/or radiation treatment.

As set forth above, a fine needle biopsy may not prove to be totally diagnostic.

The fine needle biopsy procedure involves guiding a needle in three-dimensional space under two-dimensional imaging. Accordingly, the doctor may miss the lesion, or even if he or she hits the correct target, the section of the lesion that is removed through the needle may not contain the cancerous cells or the cells necessary to assess the aggressiveness of the tumor. A needle biopsy removes enough tissue to create a smear on a slide. The device of the present invention is designed to remove the entire lesion, or a substantial portion of it, while minimizing the amount of healthy lung tissue removal. This offers a number of advantages. Firstly, the entire lesion may be examined for a more accurate diagnosis without confounding sampling error, loss of cell packing or gross architecture. Secondly, since the entire lesion is removed, a secondary procedure as described above may not be required. Thirdly, localized chemotherapy and/or energy-based tumor extirpation, such as radiation, may be introduced via the cavity created by the lesion removal.

In at least one embodiment, the invention encompasses a tissue resection mechanism comprising an outer tube having a helical coil disposed on a distal end where the coil includes a first electrode. A central tube is provided having a distal edge profile including one or more surface segments, at least one of surface segments includes a second electrode. The central tube is slidably disposed within the outer tube and is position such that the second electrode opposes at least a portion the first electrode. A cutting tube includes a cutting edge slidably disposed within the central tube and the cutting tube is configured to advance at least as far as one of the coil segments.

In another embodiment the invention encompasses a tissue resection mechanism comprising an outer tube having a helical coil disposed on a distal end where the coil includes a first electrode. A central tube is provided having a distal edge profile including one or more surface segments, at least one of surface segments includes a second electrode. The central tube is slidably disposed within the outer tube and is position such that the second electrode opposes at least a portion the first electrode. First and second ligating electrodes are disposed in the central tube and exposed to a central tube lumen. A snare is disposed in the central tube between the first and second ligating electrodes. A cutting tube includes a cutting edge slidably disposed within the central tube and the cutting tube is configured to advance at least as far as one of the coil segments.

In still another embodiment the invention encompasses a tissue resection mechanism comprising an outer tube having a helical coil disposed on a distal end where the coil includes a first electrode. A central tube is provided having a distal edge profile including one or more surface segments, at least one of surface segments includes a second electrode. The central tube is slidably disposed within the outer tube and is position such that the second electrode opposes at least a portion the first electrode. First and second ligating electrodes are disposed in the central tube and exposed to a central tube lumen. An amputation snare is disposed in the central tube and a ligation snare is disposed in the central tube. A cutting tube includes a cutting edge slidably disposed within the central tube and the cutting tube is configured to advance at least as far as one of the coil segments.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

The resection device of the present invention comprises an energy-based arrangement capable of penetrating tissue towards a target lesion. In one embodiment depicted in FIG. 1, tissue resection device 1100 includes an outer tube 1105 is provided having a distal edge profile and having an inner diameter IDouter. A coil 1110 is attached to outer tube 1105 where the coil turns are spaced from and opposed to a distal end of outer tube 1105. Coil 1110 preferably has a slightly blunted tip 1115 to minimize the possibility that it will penetrate through a blood vessel while being sufficiently sharp to penetrate tissue such as pleura and parenchyma. In some embodiments, coil 1110 may take the form of a helix having a constant or variable pitch. Coil 1110 may also have a variable cross-sectional geometry. An electrode 1130 is disposed on a surface or embedded within coil 1110.

Figure 1:
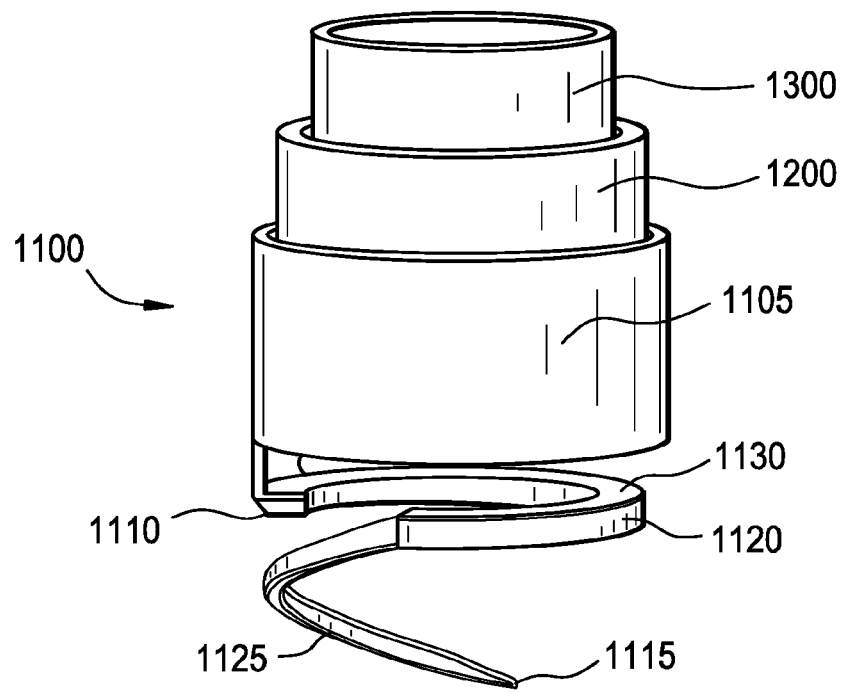
FIG. 1 depicts a tissue resection device in accordance with an embodiment of the invention.

In some embodiments, as illustrated in FIG. 1, coil 1110 may include a plurality of contiguous coil segments, e.g., coil segments 1120 and 1125. Coil segment 1120 comprises a helical member having a pitch of zero, e.g., a generally planar open ring structure, having an inner diameter IDcoil and an outer diameter ODcoil. Coil segment 1125 comprises a helical structure of constant or variable pitch and constant or variable cross-sectional geometry. In this embodiment, electrode 1130 may be disposed on a surface of or embedded in coil segment 1120.

Figure 2:
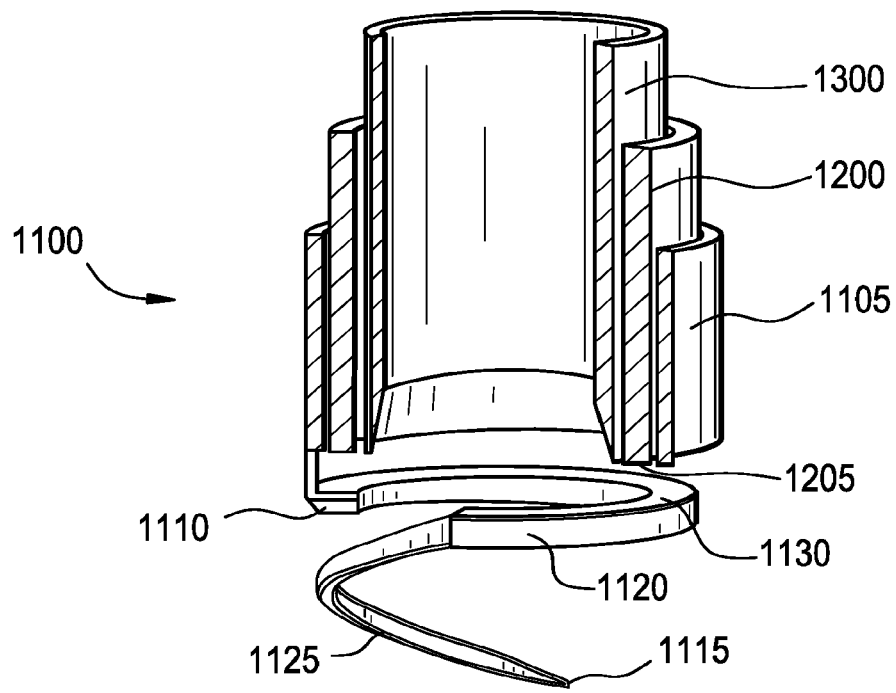
FIG. 2 illustrates a sectional view of the tissue resection device of FIG. 1.

A central tube 1200 is provided having a distal end with an edge profile comprising one or more surface segments and having an outer diameter ODcentral and an inner diameter IDcentral. As illustrated in FIG. 2, an electrode 1205 is disposed on or embedded within at least one of the surface segments. Central tube 1200 is slidably disposed within outer tube 1105 and positioned such that electrode 1205 opposes and overlaps at least a portion of electrode 1130. The space between electrode 1205 and electrode 1130 is referred to as the tissue clamping zone. In keeping with an aspect of the invention, ODcentral>IDcoil and ODcoil>IDcentral. In some embodiments, ODcentral is about equal to ODcoil. Accordingly, Central tube 1200 may be advanced through the tissue clamping zone towards coil 1110 such that electrode 1205 abuts electrode 1130.

A cutting tube 1300 is slidably disposed within central tube 1200. The distal end of cutting tube 1300 is provided with a knife edge to facilitate tissue cutting.

To enable tissue resection, the resection device 1100 may be inserted into tissue and outer tube 1105 may be advanced a predetermined distance towards a target. Coil segment 1125 allows the device to penetrate the tissue in a manner similar to a cork screw. As coil segment 1125 penetrates tissue, any vessel in its path is either moved to planar coil segment 1120 or pushed away from the coil 1100 for subsequent turns.

Coil tip 1115 is made blunt enough to minimize chances that it will penetrate through a blood vessel while still sharp enough to penetrate certain tissue such as the lung pleura and parenchyma. Central tube 1200 may then be advanced a predetermined distance towards the target. Any vessels that are disposed in the tissue clamping zone will be clamped between electrode 1130 and electrode 1205. The vessels can then be sealed by the application of bipolar energy to electrode 1130 and electrode 1205. Once blood vessels are sealed, cutting tube 1300 is advanced to core the tissue to the depth that outer tube 1105 has reached. The sealing and cutting process can be repeated to create a core of desired size.

Figure 3:
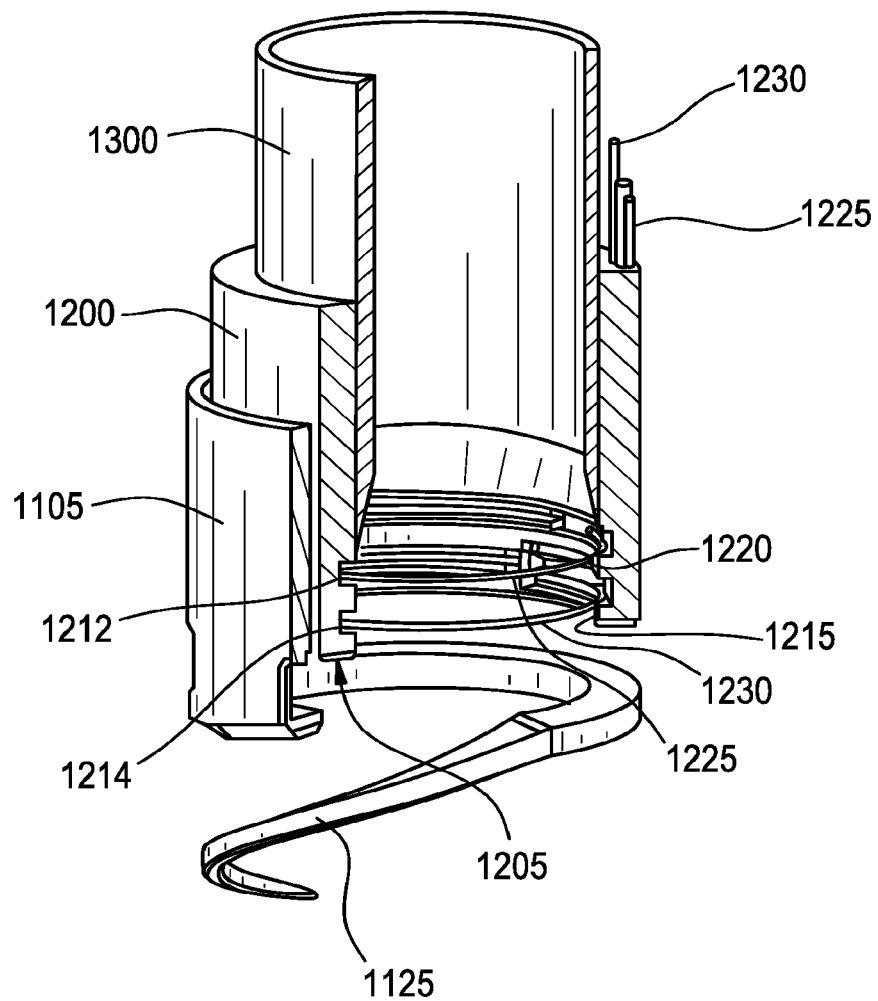
FIG. 3 shows a sectional view of a tissue resection device in accordance with an embodiment of the invention.

In keeping with an aspect of the invention, the resection device may be further configured to dissect a target lesion and seal tissue proximate the dissection point. To facilitate dissection and sealing, as illustrated in FIG. 3, central tube 1200 is provided with a ligation snare 1230, first and second ligation electrodes 1215 and 1220, an amputation snare 1225 and a ligation snare 1230. As used herein, the word "snare" refers to a flexible line, e.g., a string or a wire. The inner wall surface of central tube 1200 includes upper and lower circumferential grooved pathways 1212 and 1214 disposed proximate the distal end. The first and second ligation electrodes 1215 and 1220 are disposed on the inner wall of central tube 1200 such that lower circumferential groove 1214 is between them. Upper grooved pathway 1212 is disposed axially above ligation electrodes 1215 and 1220.

Ligation snare 1230 is disposed in lower circumferential groove 1214 and extends through central tube 1200 and axially along the outer wall surface to a snare activation mechanism (not shown). Amputation snare 1225 is disposed in upper circumferential groove 1212 and extends through central tube 1200 and axially along the outer wall surface to a snare activation mechanism (not shown). The outer surface of central tube 1200 may be provided with a plurality of axially extending grooved pathways which receive amputation snare 1225, ligation snare 1230 and are in communication with upper and lower circumferential grooved pathways 1212 and 1214. In addition, electrode leads for ligation electrodes 1215 and 1220 may extend to an energy source via the axially extending grooved pathways.

In operation, the resection device of this embodiment can detach and seal the tissue core. Cutting tube 1300 may be retracted to expose ligation snare 1230 which is preferably made of flexible line, e.g., suture. Ligation snare 1230 may be engaged to snag tissue and pull tissue against the inner wall surface between first and second ligation electrodes 1215 and 1220. Bipolar energy is then applied to first and second electrodes 1215 and 1220 to seal, i.e., cauterize, the tissue. Once sealed, cutting tube 1300 may be further retracted to expose amputation snare 1225 which may then be activated to sever the tissue core upstream from the point where the tissue was sealed (ligation point). In some embodiments, amputation snare 1225 has a smaller diameter than that of ligation snare 1230. The smaller diameter facilitates tissue slicing. Accordingly, the resection device 1100 according to this embodiment both creates a tissue core and disengages the core from surrounding tissue.

In an alternative embodiment, the resection device of the invention is provided with a single snare disposed between ligation electrodes which both ligates and cuts tissue. In this embodiment, the single snare first pulls tissue against the inner wall surface of central tube 1200 between ligation electrodes 1215 and 1220. Bipolar energy is then applied to first and second electrodes 1215 and 1220 to seal, i.e., cauterize, the tissue. Once sealed, the snare is further pulled to sever the tissue core.

Figure 4:
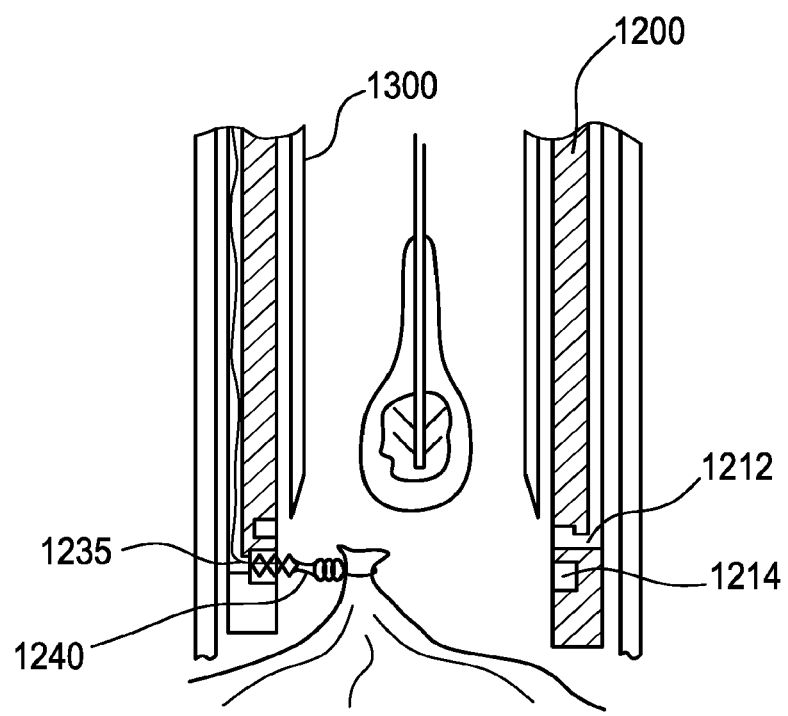
FIG. 4 depicts a sectional view of a tissue resection device in accordance with an embodiment of the invention.

In yet another embodiment, cutting and sealing may be performed without employing electrodes. In this embodiment, ligation snare 1230 includes a set of knots 1235 and 1240 which tighten under load, shown, for example, in FIG. 4. Ligation is performed by retracting cutting tube 1300 to expose ligation snare 1210 and activating ligation snare 1230 which lassos tissue as ligation knot tightens. Once the tissue is lassoed, cutting tube 1300 may be further retracted to expose amputation snare 1225 which may then be activated to sever the tissue core upstream from the point where the point where the tissue was lassoed.

The present invention also contemplates a method and system for using the resection device to remove tissue lesions, for example, lung lesions. The method generally comprises anchoring the lesion targeted for removal, creating a channel in the tissue leading to the target lesion, creating a tissue core which includes the anchored lesion, ligating the tissue core and sealing the surrounding tissue, and removing the tissue core including the target lesion from the channel.

Anchoring may be performed by, any suitable structure for securing the device to the lung. Once the lesion is anchored, a channel may be created to facilitate insertion of resection device 1100. The channel may be created by making an incision in the lung area and inserting a tissue dilator and port into the incision. A tissue core which includes the anchored lesion may be created. In keeping with the invention, resection device 1100 may be inserted into the channel and used to create the tissue core, to ligate the tissue core and to seal the tissue core and sever it from the surrounding tissue as described hereinabove. The tissue core may then be removed from the channel. In keeping with the invention, a cavity port may be inserted in the channel to facilitate subsequent treatment of the target lesion site through chemotherapy and/or energy-based tumor extirpation such as radiation.

Figure 5:
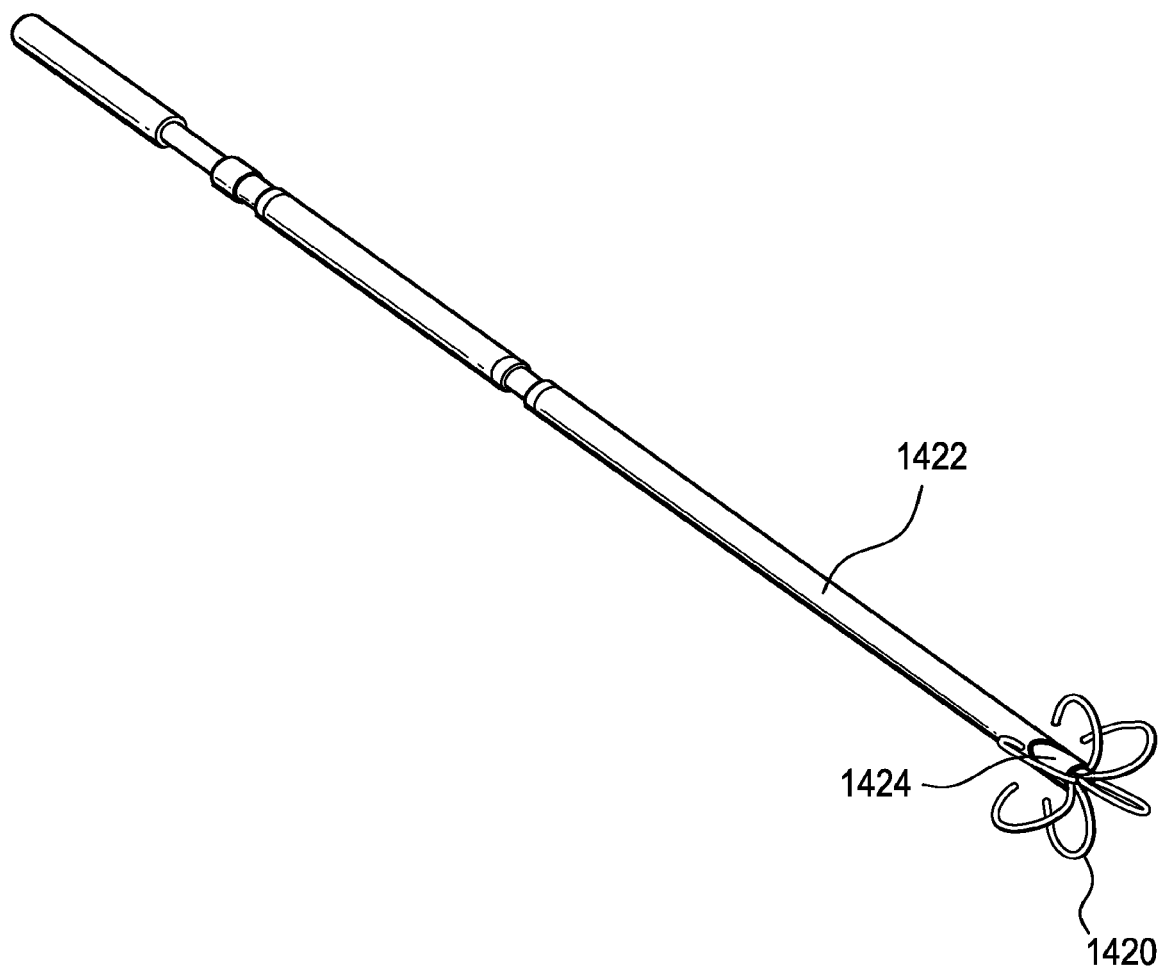
FIG. 5 illustrates an exemplary anchor that may be employed in a lesion removal method in accordance with an embodiment of the invention.

The anchor depicted in FIG. 5 is suitable for use in performing the method for removing tissue lesions described herein. The anchor comprises an outer tube 1422 having a sufficiently sharp edge to pierce the chest cavity tissue and lung without causing excess damage and an inner tube 1424 disposed within outer tube 1422. One or more tines or fingers 1426 formed from shape memory material, e.g., Nitinol, preformed are attached to the end of inner tube 1424. Outer tube 1422 is retractably disposed over inner tube 1424 such that when outer tube 1422 is retracted, tines 1426 assume their preform shape as shown. In keeping with the invention, outer tube 1422 is retracted after it has pierced the lung lesion thereby causing tines 1426 to engage the lung lesion. Other suitable anchors may include coils and suction-based structures.

Figure 6:
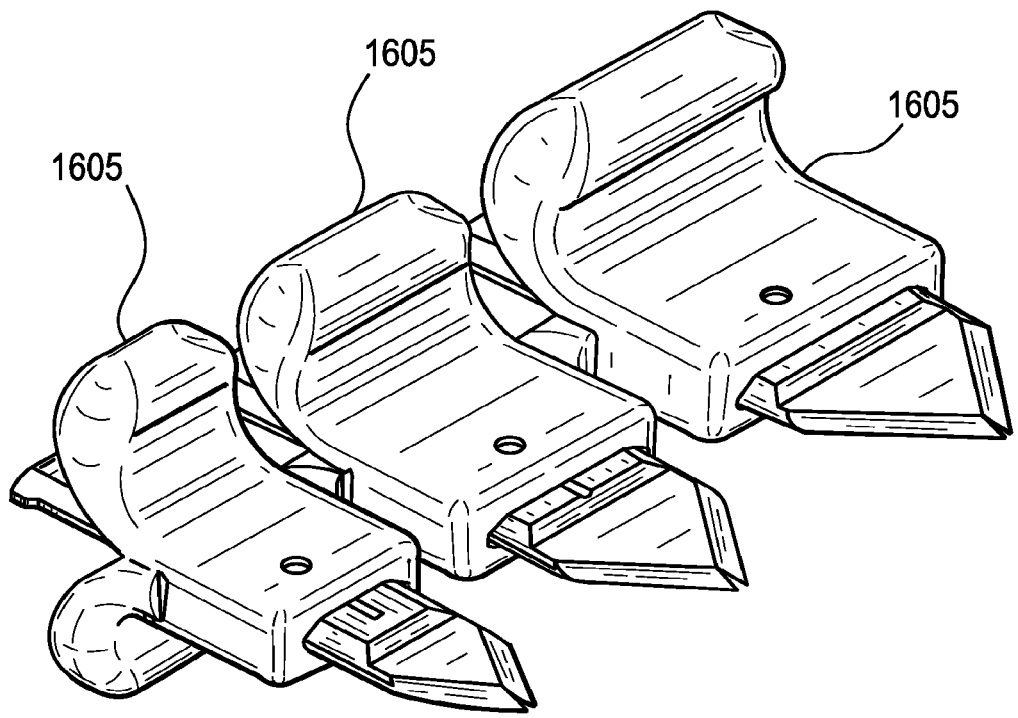
FIG. 6 shows a series of incision blades for use in a lesion removal method in accordance with an embodiment of the invention.

The incision blades depicted in FIG. 6 are suitable for use in performing the method for removing tissue lesions described herein. Once anchor 1400 is set, it is preferable to create a small cut or incision to facilitate insertion of chest wall tissue dilator. Incision blades 1605 are used to make a wider cut. Successive incision blades 1605 include a central aperture which allows them to be coaxially advanced along the anchor needle 1405 to create a wider cut in the chest wall, with each successive blade being larger than the previous blade, thereby increasing the width of the incision.

Figure 7:
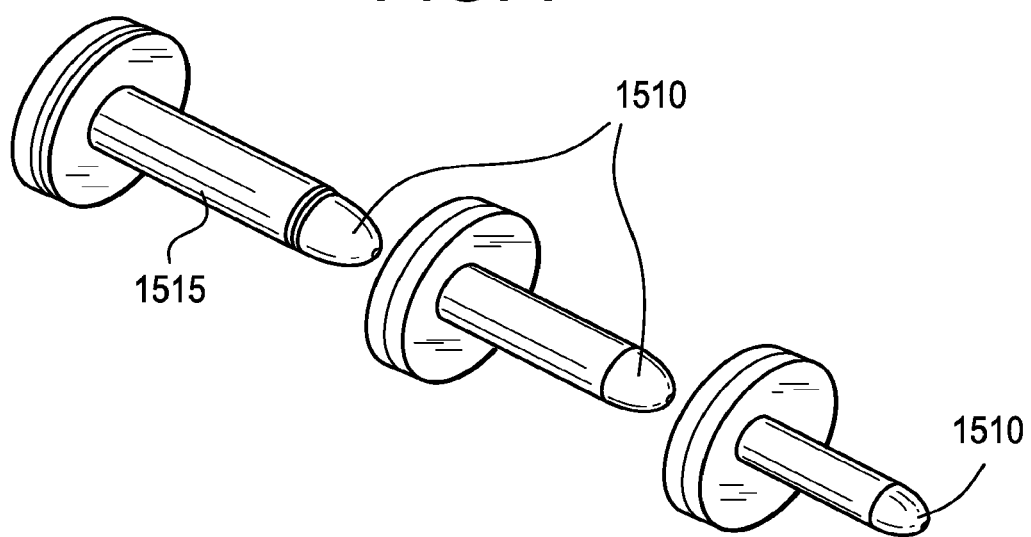
FIG. 7 displays tissue dilators suitable for use in a lesion removal method in accordance with an embodiment of the invention.

The tissue dilator depicted in FIG. 7 is suitable for use in performing the method for removing tissue lesions described herein. The tissue dilator may comprise any suitable device for creating a channel in organic tissue. In one exemplary embodiment, the tissue dilator assembly includes a single cylindrical rod with rounded end 1510 or a cylindrical rod with rounded end and a rigid sleeve arrangement 1515. Successive tissue dilators are coaxially advanced along the anchor needle to create tissue tract or channel in the chest wall, with each successive dilator being larger than the previous dilator, thereby increasing the diameter of the channel. Once the final dilator with rigid sleeve is deployed, the inner rod 1505 is removed while leaving the rigid sleeve in the intercoastal space between ribs to create direct passage to the lung pleura.

Any tissue resection device capable of penetrating lung tissue and creating a tissue core including a target lesion is suitable for use in performing the method for removing tissue lesions described herein. Tissue resection device 1100 described hereinbefore is preferred.

Once tissue resection device 1100 is removed, a small channel in the lung exits where the target lesion was removed. This channel may be utilized to introduce an energy-based ablation device and/or localized chemotherapy depending on the results of the tissue diagnosis. Accordingly, the method and system of the present invention may not only be utilized to ensure an effective biopsy is performed but also complete removal of the lesion with minimal healthy lung tissue removal.

Although shown and described is what is believed to be the most practical and preferred embodiments, it is apparent that departures from specific designs and methods described and shown will suggest themselves to those skilled in the art and may be used without departing from the spirit and scope of the invention. For example, the systems, devices and methods described herein for removal of lesions from the lung. It will be appreciated by the skilled artisan that the devices and methods described herein may be not limited to the lung and could be used for tissue resection and lesion removal in other areas of the body. The present invention is not restricted to the particular constructions described and illustrated, but should be constructed to cohere with all modifications that may fall within the scope of the appended claims.

What is claimed is:

1. An apparatus, comprising:
a coil including a planar portion;
a first electrode disposed on a proximal surface of the planar portion of the coil;
a second electrode arranged proximal to the first electrode and configured to oppose at least a portion of the first electrode such that the first and second electrodes define a clamping zone therebetween,
the first and second electrodes configured to apply energy to seal at least some vessels in tissue disposed in the clamping zone; and
a cutting tube including a distal cutting edge, the cutting tube configured to be advanced at least as far as a segment of the coil to cut at least a portion of the tissue disposed in the clamping zone.

2. The apparatus of claim 1, wherein the coil is a helical coil that includes a first coil segment and a second coil segment that are contiguous.

3. The apparatus of claim 2, wherein the first coil segment includes a planar open ring.

4. The apparatus of claim 2, wherein the first coil segment includes a planar open ring, and the second coil segment includes a helical structure having a constant or variable pitch.

5. The apparatus of claim 2, wherein the first coil segment has a first pitch and the second coil segment has a second pitch different from the first pitch.

6. The apparatus of claim 1, wherein the vessels are blood vessels, and the coil includes a blunt tip configured to penetrate through tissue distal to the coil without penetrating through the blood vessels disposed therein.

7. The apparatus of claim 6, wherein the tissue includes lung tissue, and the blunt tip of the coil is configured to penetrate through pleura and parenchyma of the lung tissue without penetrating through the blood vessels disposed therein.

8. The apparatus of claim 1, further comprising a tube having a distal surface segment, the second electrode being disposed on the distal surface segment.

9. The apparatus of claim 1, wherein the first electrode and the second electrode are a first set of electrodes, the apparatus further comprising:
a snare element configured to pull at least a portion of tissue disposed near the clamping zone toward a second set of electrodes configured to apply energy to seal the pulled tissue,
the snare element further configured to sever at least a portion of the tissue.

10. The apparatus of claim 9, wherein the snare element includes a flexible line.

11. An apparatus, comprising:
a first electrode;
a second electrode;
a coil including a plurality of coil segments, the plurality of coil segments including a planar coil segment and a helical coil segment, the first electrode disposed on at least a portion of the planar coil segment;

a tube, the second electrode disposed on a distal end of the tube, the distal end of the tube configured to be advanced through a clamping zone toward the planar coil segment such that the first and second electrodes clamp a portion of tissue therebetween, the first and second electrodes configured to apply energy to seal at least some vessels in the portion of tissue clamped between the first electrode and the second electrode; and a cutting tube including a distal cutting edge, the cutting tube configured to be advanced to at least one of the plurality of coil segments to cut at least a portion of the tissue disposed in the clamping zone.

12. The apparatus of claim 11, wherein the planar coil segment includes a planar open ring.

13. The apparatus of claim 11, wherein the helical coil segment has a constant or variable pitch.

14. The apparatus of claim 11, wherein the vessels are blood vessels, and the coil includes a blunt tip configured to penetrate through tissue distal to the coil without penetrating through the blood vessels disposed therein.

15. The apparatus of claim 14, wherein the tissue includes lung tissue, and the blunt tip is configured to penetrate through pleura and parenchyma of the lung tissue without penetrating through the blood vessels disposed therein.

16. The apparatus of claim 11, wherein the second electrode is disposed on a distal surface segment of the tube.

17. The apparatus of claim 11, wherein the first electrode and the second electrode are a first set of electrodes, the apparatus further comprising:

a snare element configured to pull at least a portion of tissue disposed in the tube toward a second set of electrodes configured to apply energy to seal the pulled tissue, the snare element further configured to sever at least a portion of the tissue.

18. The apparatus of claim 17, wherein the snare element includes a flexible line.

19. The apparatus of claim 17, further comprising a groove, the snare element being disposable within the groove.

20. An apparatus, comprising:

an outer tube having a helical coil disposed on a distal end, the helical coil including a first electrode;

a central tube having a distal edge profile including one or more surface segments, at least one of the surface segments including a second electrode, the central tube configured to be movable relative to the outer tube such that the central tube can be positioned relative to the outer tube with the second electrode opposing at least a portion of the first electrode to clamp a portion of tissue therebetween;

the first and second electrodes configured to apply energy to seal at least some vessels in the portion of tissue tissue disposed between the first and second electrodes; and a cutting tube including a distal cutting edge, the cutting tube configured to be advanced to a segment of the helical coil to cut at least a portion of the tissue.

21. The apparatus of claim 20, wherein the helical coil includes a planar coil segment and a helical coil segment that are contiguous, the planar coil segment including the first electrode.

22. The apparatus of claim 21, wherein the planar coil segment includes a planar open ring.

23. The apparatus of claim 21, wherein the helical coil segment has a constant pitch.

24. The apparatus of claim 21, wherein the helical coil segment has a variable pitch.

25. The apparatus of claim 21, wherein the planar coil segment has (1) an inner diameter that is less than an outer diameter of the central tube and (2) an outer diameter that is greater than an inner diameter of the central tube.

26. The apparatus of claim 21, wherein the planar coil segment has an outer diameter that is substantially equal to an outer diameter of the central tube.

27. The apparatus of claim 20, wherein the vessels are blood vessels, and the coil includes a blunt tip configured to penetrate through tissue distal to the coil without penetrating through the blood vessels disposed therein.

28. The apparatus of claim 20, wherein the first and second electrodes have surface profiles that are substantially matching.

29. The apparatus of claim 20, wherein the first electrode and the second electrode are a first set of electrodes, the apparatus further comprising:

A snare element configured to pull at least a portion of tissue disposed in the central tube toward a second set of electrodes configured to apply energy to seal the pulled tissue, the snare element further configured to sever at least a portion of the tissue.

* * * * *